United States Patent [19]

Haber et al.

[11] Patent Number: 5,256,413
[45] Date of Patent: Oct. 26, 1993

[54] METHOD AND USE FOR SITE-SPECIFIC ACTIVATION OF SUBSTANCES

[75] Inventors: Edgar Haber, Weston; Gary R. Matsueda, Winchester, both of Mass.

[73] Assignee: The General Hospital Corporation, Boston, Mass.

[21] Appl. No.: 946,015

[22] Filed: Sep. 15, 1992

Related U.S. Application Data

[63] Continuation of Ser. No. 498,470, Mar. 26, 1990, abandoned, which is a continuation of Ser. No. 774,469, Sep. 10, 1985, abandoned, which is a continuation of Ser. No. 689,851, Jan. 8, 1985, Pat. No. 5,116,613.

[51] Int. Cl.$^5$ ............. A61K 39/395; C07K 15/28
[52] U.S. Cl. ............. 424/85.8; 435/70.21; 435/172.2; 435/188; 435/240.27; 530/382; 530/388.25; 530/389.3; 530/391.7; 935/104; 935/107
[58] Field of Search ............. 424/85.8, 85.91; 530/380, 382, 388.25, 389.3, 391.7; 514/2; 935/104, 107; 435/70.21, 172.2, 240.27, 188

[56] References Cited

U.S. PATENT DOCUMENTS

| | | | |
|---|---|---|---|
| 4,368,149 | 1/1983 | Masuho et al. | 530/390 |
| 4,414,148 | 11/1983 | Jansen et al. | 530/389 |
| 4,545,988 | 10/1985 | Nakayama et al. | 424/94 |
| 4,671,958 | 6/1987 | Rodwell et al. | 530/388 |
| 4,673,573 | 6/1987 | Ferres et al. | 424/85 |
| 4,722,903 | 2/1988 | Kudryk et al. | 435/172.2 |
| 4,916,070 | 4/1990 | Matsueda et al. | 435/172.2 |
| 4,927,916 | 5/1990 | Matsueda et al. | 530/387 |

FOREIGN PATENT DOCUMENTS 0142905  5/1985  European Pat. Off.

OTHER PUBLICATIONS

Rajagopalan et al, J. Clin. Invest., 75, 413-19, (Feb. 1985).
Collen et al, J. Clin. Invest., 71, 368-76, (1983).
McCabe et al, Cancer. Res., 5886-93, 44, (Dec. 1984).
Kudryk et al, Mol. Immunol., 21(1), 89-94, (Jan. 1984).
Sharma et al, N.E.J.M., 306(21), 1268-76, (1982).
Hui et al, Science, 222, 1129-31, (Dec. 1983).
Sevilla et al, Fed Proceedings, #3872, p. 1073, (Mar. 5, 1985).
Bode et al., Science 229: 765-767 (1985).
Philpott et al., Jour. Immunols. 125: 1201-1209 (1980).
Philpott et al., Jour. Immunol. 111: 921-929 (1973).
Matsueda et al., Proceedings, 8th Amer. Peptide Sympos., Tucson, Ariz. May 1983, publication Jan. 1984.
Matsueda et al., Proceedings: Fibrinogen and its Degradation Products, Stockholm (1983), publication Jan. 1984.
Matsueda et al., Federation Proceedings 42(7):Abs. 1375 (1983).

Primary Examiner—David L. Lacey
Assistant Examiner—Robert D. Budens
Attorney, Agent, or Firm—Sterne, Kessler, Goldstein & Fox

[57] ABSTRACT

Disclosed is a method for the in vivo lysis of a thrombus in a host by administration of a conjugate consisting of a monoclonal antibody specific for fibrin coupled to a plasminogen activator such as tissue plasminogen activator, urokinase or streptokinase.

2 Claims, 2 Drawing Sheets

METHOD AND USE FOR SITE-SPECIFIC ACTIVATION OF SUBSTANCES

CROSS REFERENCE TO RELATED APPLICATION

The present application is a continuation of Ser. No. 07/498,470, filed Mar. 26, 1990, now abandoned, which is a continuation of Ser. No. 06/774,469, filed Sep. 10, 1985, now abandoned, which is a continuation-in-part of Ser. No. 06/689,851, Jan. 8, 1985, now U.S. Pat. No. 5,116,613, issued May 26, 1992, which disclosures are herein incorporated by reference.

BACKGROUND OF THE INVENTION

1. Field of the Invention

The present invention relates to a method for activating an inactive substance at a specific site in a human or other animal.

2. Background of the Invention

The use of antibodies for passive immunization has been utilized for many years. Early attempts using this methodology usually involved the administration of antibodies specific for a disease agent, which were raised in another species and later administered to the recipient which was a member of a different species. This approach proved to be of limited value from the standpoint of effectiveness as well as from the perspective of adverse reactions by the host to the large quantities of foreign antibody protein which had to be administered to achieve significant therapeutic effect. As a consequence, the individual of the species receiving the passively administered antibodies would often develop an adverse reaction to these foreign proteins, resulting in what is commonly known as serum sickness.

Another serious drawback to the early attempts at passive immunotherapy was the poor specificity, or selectivity, of the antibodies that were produced by the source species. Many times the species in which the antibody was produced recognized antigenic determinants and produced antibodies thereto which would react with non-protective determinants on the pathogenic agent in the recipient species or, even worse, would cross-react with the normal tissues of the recipient species. Additionally, because the percentage of antibodies which were therapeutically effective was often quite small compared to the total amount of antibody produced by the source species, and because there was no effective means of separating the useful antibodies from those which were not, the recipient species had to be exposed repeatedly to large quantities of antibody protein in order to receive a protective amount of the useful antibody. Often this repeated exposure of the recipient species to these large quantities of foreign antibody would cause the recipient's own immune system to attack these foreign proteins, resulting in greatly decreased therapeutic effectiveness and serum sickness. As a result of these complications, the use of passive immunotherapy in the past has been extremely limited.

In recent years, interest in the use of passive immunotherapy has been restimulated by the development of monoclonal antibody technology. Because of the nature of this technology, it is now possible to produce antibodies to substances which in the past were not sufficiently immunogenic for purposes of polyclonal antibody production and actually select the antibody that has the desired therapeutic specificity. In addition, since these antibodies are produced by a single clone responding to stimulation by a single epitopic determinant, the high degree of site specific selectivity that can be achieved makes it conceivable that much lower concentrations of passively administered antibody may now be used.

Early clinical investigators quickly realized the advantages of this technology and endeavored to utilize monoclonal antibodies which were specific for the site of disease in the host, but would not cross-react with normal host tissue. This great specificity, in turn, enabled scientists to couple monoclonal antibodies to highly toxic drugs or radioactive substances which in the past could not effectively be utilized because of the toxic side effects to the host when the substances were administered systemically. However, a potential danger inherent in this approach to passive immunotherapy using monoclonal antibodies coupled to an active toxic substance, is that these active substances may become uncoupled from the monoclonal antibody and thus pose a toxic threat to the host. The method according to the present invention circumvents these earlier problems by coupling a relatively non-toxic substance, the activator, to an antibody specific for the target site.

Although in many instances highly effective drugs have been developed for treatment of various disease states, their toxic side effects at concentrations necessary to achieve therapeutic effectiveness often negates their usefulness.

One specific problem of lack of selectivity relates, for example, to thrombolytic agents used to dissolve blood clots.

Coronary arteriographic studies indicate that 90–95% of transmural myocardial infarctions are caused by coronary thrombosis (DeWood, M. A. et al., N. Eng. J. Med., 303:897–902 (1983)). Although thrombolytic agents currently available can lyse coronary artery thrombi in the early hours of coronary thrombosis and thereby diminish myocardial injury, their clinical application has been attended by significant problems. These agents are activators of the precursor plasminogen which is activated to the fibrinolytic enzyme plasmin. Plasmin is non-selective and not only effects lysis of the fibrin in the thrombus, but also promotes generalized fibrinogenolysis, at times resulting in severe bleeding (Laffel, G. L. et al., ibid, 311:710–717 and 770–776 (1984)). Human tissue plasminogen activator may be more fibrin-specific, but bleeding complications have nevertheless been observed.

Currently, two activators are commercially available, streptokinase and urokinase. Both are indicated for the treatment of acute cardiovascular disease such as infarct, stroke, pulmonary embolism, deep vein thrombosis, peripheral arterial occlusion, and other venous thromboses. Collectively, these diseases account for major health hazards and risks. Streptokinase and urokinase, however, have severe limitations. Neither has a high affinity for fibrin; consequently, both activate circulating and fibrin-bound plasminogen relatively indiscriminately. In addition, the plasmin formed in circulating blood is neutralized rather quickly and its efficacy lost for useful thrombolyses. Residual plasmin will degrade several clotting factor proteins, for example, fibrinogen, factor V and factor VIII, causing hemorrhagic potential. In addition, streptokinase is strongly antigenic and patients with high antibody titers respond inefficiently to treatment and cannot remain on continuous treatment. The recent availability of human tissue-type plasminogen activator has somewhat improved the therapeutic prospects. Nevertheless, the issue of selectivity remains an important one.

SUMMARY OF THE INVENTION

One way to avoid systemic exposure to highly active, non-selective, and particularly toxic agents would be by selectively activating the agent at the target site where its therapeutic effect can be maximized. The fact that the drug can be selectively concentrated at the target site would require minimal exposure of the host to the active agent and diminution of side effects associated with systemic exposure.

In order to provide a more selective means for administering drugs, the inventors have thus conceived and developed a method whereby antibodies which are specific for the site of disease in a host are bound to an activator. When these antibodies are administered to the host, they specifically bind to the disease target site having the epitope for which these antibodies are specific. The antibody-bound activator then reacts with an inactive substance also present in the host and converts the inactive substance to an active substance which, because of its proximity or affinity for the target site, reacts with the target site. This inactive substance may be exogenous or endogenous to the host system in which the target site is located.

Thus, the present invention provides a method for a host site-specific activation of an inactive substance, which comprises:
(a) causing the contact of a host target site with an antibody specific for an epitope on said target site, wherein said antibody is bound to an activator of said inactive substance, to thereby bind said antibody to said epitope; and
(b) causing the contact of said inactive substance with said antibody-bound activator, thereby activating said inactive substance towards reaction with said target site.

The invention also includes products for use in the aforementioned method, such as a product comprising a host target site-specific antibody substantially devoid of cross-reactivity to non-target site tissue, coupled to an activator of an inactive substance capable of being activated by said activator to a substance which is physiologically active towards said target site.

A particular embodiment of the invention comprises powerful and selective complex thrombolytic products which have an increase in selectivity over prior art thrombolytic agents. These products are obtained by providing:

a fibrin-specific antibody substantially devoid of fibrinogen cross-reactivity coupled to an agent causing thrombolysis.

The invention also relates to methods of lysing a thrombus by bringing said thrombus in contact with a lysing amount of the antibody/thrombolytic product mentioned above.

Pharmaceutical compositions comprising the products together with pharmacologically appropriate carriers are also included in this invention.

BRIEF DESCRIPTION OF THE PREFERRED EMBODIMENTS

Figure 1:
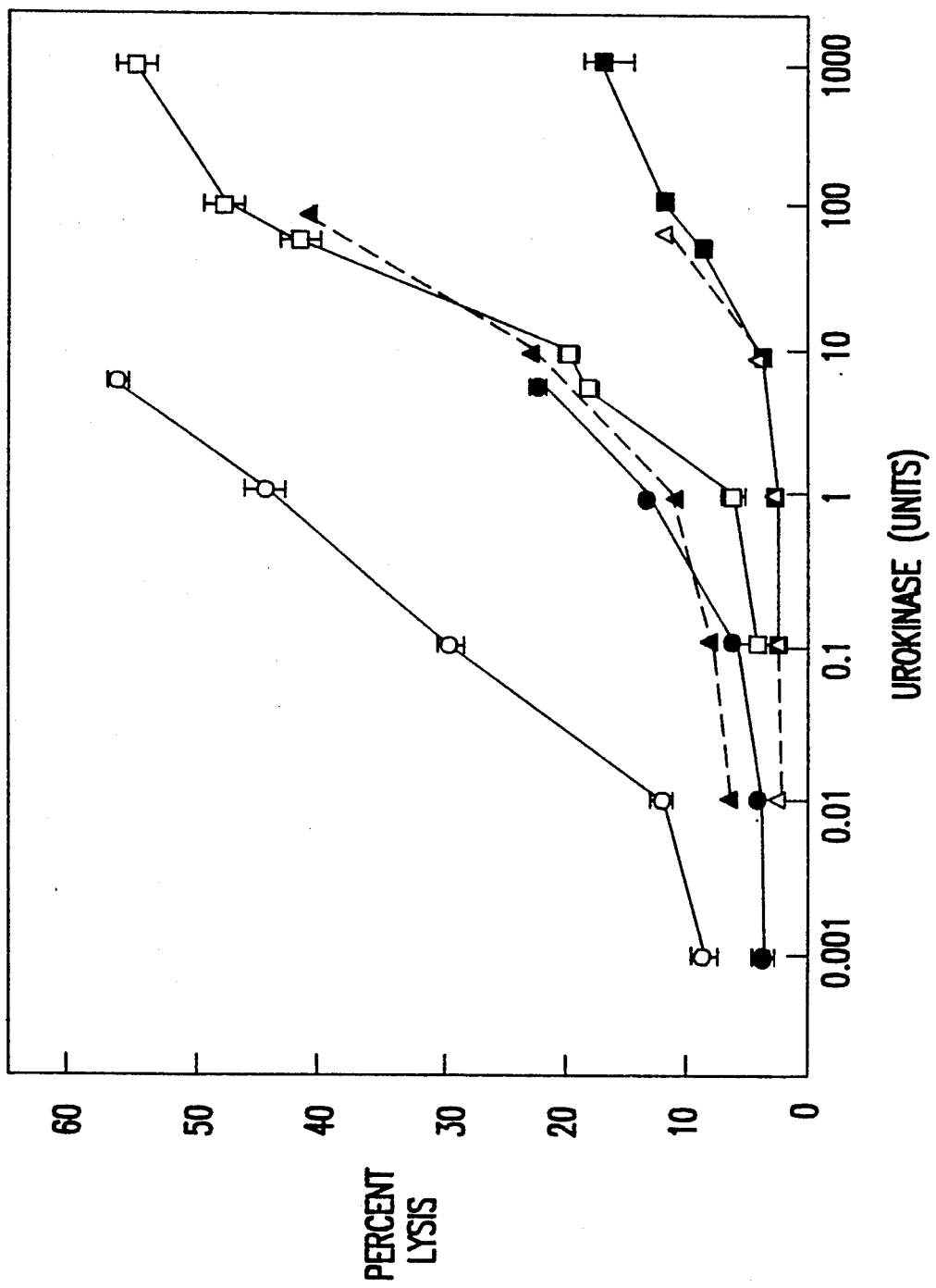
FIG. 1 shows the release of labeled peptides from fibrin-Sepharose by a conjugate of urokinase and fibrin-specific antibody (●, 2.5 hours; ○, 15 hours), urokinase myosin antibody conjugate (Δ, 2.5 hours; ▲, 15 hours), and unconjugated urokinase (■, 2.5 hours; □, 15 hours). Conjugated or unconjugated urokinase (100 ul containing the indicated amount of urokinase) were incubated for 4 hours with 100 ul $^{125}I$ fibrin-Sepharose, washed with 1×3 ml 0.1M Tris, 0.1M NaCl, 0.5% BSA, 0.5% Triton ×100 and 3×3 ml TBSA, and incubated for 2.5 and 15 hours with purified plasminogen (120 mg/l). Lysis was expressed as the quotient of released radioactivity and total radioactivity. Each point represents the mean standard±deviation of three independent determinations.

In the method according to the invention, an antibody bound to an activator and specific for an epitope or epitopes present on a target site in a host system is administered to the host system and allowed to bind to specific epitopes at the target site. The bound activator then activates an inactive substance which thereby becomes activated and reacts with or is absorbed by the target site. The inactive substance may be either exogenous or endogenous to the host system in which the target site is located.

In other words, the target site is a target for both the specific antibody and the activated substance. For example, the target site may be a protein capable of being bound by the specific antibody and of being a substrate for the activated substance when the activated substance is a proteolytic enzyme.

The antibodies which can be used in the present invention may be any antibodies which are specific for determinants on the target site. For example, Shouval et al. (*Proc. Natl. Acad. Sci. U.S.A.*, 79:650 (1982)) have described monoclonal antibodies specific for hepatoma cells, but which show low reactivity with normal host tissue.

Examples of other target sites and non-target sites which can be differentiated using specific antibodies are listed in Table I.

TABLE I

| Factors Differentiated by Specific Antibody | Reference |
|---|---|
| Epitopes of Gamma-Interferon | Chang et al., Proc. Natl. Acad. Sci., USA 81:5219 (1984) |
| Forms of Collagen | Linsenmeyer et al., J. Cell. Biol. 96:124 (1983) |
| Lysozymes of Different Species | Metzger et al., Eur. J. Immunol. 14:87 (1984) |
| Proinsulin and Insulin | Madsen et al., Diabetes 33:1012 (1984) |
| Hemoglobins of Different Species | Stamatoyannopoulos et al., Blood 61:530 (1983) |
| Variations in Amino Acid Sequence of Angiotensin II | Nussberger et al., Hybridoma 3:373 (1984) |
| Variations in Structure of Digoxin | Hunter et al., J. Immunol. 129:1165 (1982) |
| Colorectal Carcinoma Cells from Normal Colon Cells | Herlyn et al., Proc. Natl. Acad. Sci., USA, 76:1438 (1979) |
| Metastatic Lymph Node Cells | Weinstein, et al., Science, |

TABLE I-continued

| Factors Differentiated by Specific Antibody | Reference |
|---|---|
| from Normal Lymph Node Cells | 222:423 (1983) |
| Malignant Melanoma Cells from Nonmalignant Cells | Steplewski, et al., Eur. J. Immunol., 9:94 (1979) |
| Lymphoma Cells from Normal Lymphoid Cells | Nadler, et al., J. Immunol., 125:570 (1980) |

The target site, which has epitopes that allow the antibody of the invention to bind, may be any site for which it is deemed that initiation of therapy is appropriate. Such sites may be those arising from a pathogenic state induced by, for instance, a virus or a bacteria; a tumor; or the result of a dysfunction of a normal host system as, for example, the formation of a thrombus.

The term "tumor" denotes any abnormal proliferation of tissues which differ in their genotypic or physical composition from that part of the body in which the tumor grows. Such tumor growth may be either benign or malignant in its nature. A benign tumor is one that is presently of a non-life threatening nature, whereas a malignant tumor is one that has a tendency to progressively worsen and may result in death.

The term "causing the contact" as used in the present invention is meant to encompass the exposure of the target site to the activator-bound antibody which is essentially specific for the target site.

The term "epitope" as used in this invention is meant to include any determinant responsible for specific interaction with an antibody molecule. Epitopic determinants usually consist of chemically active surface groupings of molecules such as amino acids or sugar side chains and have specific three dimensional structural characteristics as well as specific charge characteristics.

The term "target-site" denotes any region to which it is desirable to bind the activator-bound site-specific antibody.

It is to be understood that the term "bound" as applied to the attachment of the activator to the target site-specific antibody means that the activator and antibody are bound in such a manner that the activator remains capable of activating the inactive substance and the antibody remains capable of reacting with the target site.

The activator which is bound to the target site-specific antibody is a substance or agent which will react with an inactive substance to convert the inactive substance into an active substance. This activating factor may activate the inactive substance by such means as, for example, reacting chemically, allosterically, or enzymatically with the inactive substance. It is not necessary that this activation be 100% as long as it is substantial enough to achieve some activity.

Chemical activators can be those which react in a manner to cleave or remove a chemical moiety or alteration on the inactive substance when this moiety or alteration is the cause of the inactivation. The cleavage or removal of this inactivating moiety would activate the inactive substance so that it could then react or be absorbed by the target site.

An allosteric activator would be an agent which binds to a region on the inactive substance distant from the region on the inactive substance that reacts with the target site after activation of the inactive substance. Upon binding of the allosteric activator to its binding region, the inactive substance is converted into an active substance capable of reacting with the target site.

Streptokinase is an example of an allosteric activator. Streptokinase has no intrinsic activity, but upon complexation with plasminogen, which also is inactive, a conformational change occurs which activates plasminogen. The activated plasminogen can then serve as an activator of other plasminogen molecules (Jackson et al., Biochemistry, 21:6620 (1982)). Other examples of allosteric activators include staphylokinase (Lack et al., Methods in Enzymology, 19:706 (1970)) and staphylocoagulase (Hamker et al., Biochemica Biophysica Acta, 379:180 (1975)).

It is also possible for the activator to be an enzyme which would react enzymatically with a proenzyme to produce an active enzyme, which can then react with or be absorbed by the target site. Examples of enzymes that can be used in this manner are listed in Table II.

TABLE II

| Activator | Inactive Substance (Proenzyme) | Active Substance (Enzyme) | Target Site (Substance) |
|---|---|---|---|
| Trypsin | Chymotrpysinogen | Chymotrypsin | Protein |
| Urokinase | Plasminogen | Plasmin | Fibrin |
| Trypsin | Procarboxy-peptidase | Carboxy-peptidase | Protein Protein |
| Enterokinase | Trypsinogen | Trypsin | Protein |
| Proaccelerin | Prothrombin | Thrombin | Fibrinogen |
| Streptokinase | Plasminogen | Plasmin | Fibrin |

The inactive substance as described in the invention may be either exogenous or endogenous to the host system. In either case, in the presence of the activator-bound antibody which is present at the target site, the inactive substance is converted to an active substance which then reacts therapeutically or otherwise with the target site for the benefit of the host system.

The inactive substance may be modified or unmodified. For example, when the substance is modified the host system may be exposed to, for example, a toxin which has been modified with a blocking group such that it is no longer toxic. In the presence of an antibody-bound chemical activator, the blocking group is removed and the inactive toxin becomes activated in the proximity of the target site so that the toxic substance reacts with the target site. Examples of bacterial toxins that can be utilized in this manner are listed in Table III.

TABLE III

| Organism/Toxin (Active Substance) | Action |
|---|---|
| *Clostridium perfringens* | |
| alpha | lecithinase: necrotizing, hemolytic |
| epsilon | nectrotizing |
| iota | necrotizing |
| lambda | proteolytic |
| *Clostridium novyi* | |
| alpha | necrotizing |
| beta | lecithinase: necrotizing, hemolytic |
| gamma | lecithinase: necrotizing, hemolytic |
| epsilon | lipase: hemolytic |
| *Corynebacterium diptheriae* diphtheritic toxin | enzyme altering transferase |
| *Staphylococcus aureus* gamma | necrotizing, hemolytic |
| *Bordetella pertussis* whooping cough toxin | necrotizing |
| Pseudomonas | inhibits protein synthesis |

TABLE III-continued

| Organism/Toxin (Active Substance) | Action |
|---|---|
| exotoxin A | |
| *Shigella dysenteriae* shiga toxin | proteolytic |

It is also possible for the exogenous inactivated substance to be unmodified. In this situation, the exogenous substance may be, for example, a proenzyme which normally is not present in the host system and which, when reacted with the activator, is converted to an active enzyme which, in turn, reacts with substrate present at the target site.

In another embodiment, it is possible for the inactive substance to be endogenous to the host system in which the target site is located and which, in the presence of the activator, is converted to an active form which reacts with, or is absorbed by, the target site. An example of an endogenous inactive substance would be a pro-enzyme such as, for example, plasminogen which, in the presence of the activator such as, urokinase is converted to the active enzyme plasmin which can then react with a target site containing fibrin.

The antibodies which can be used in the invention should be specific for an epitope on the target site and essentially non-reactive with epitopes of tissues not present at the target site.

If polyclonal antibodies are used, it may be necessary to purify them using affinity chromatography to achieve the desired degree of target site specificity. For example, purification of essentially target site-specific polyclonal antibody could be achieved by:

(a) firmly binding target site material, or an extract thereof, to a carrier;
(b) binding the polyclonal antibody specific for the target site;
(c) washing the bound polyclonal antibody;
(d) eluting the bound polyclonal antibody from the target site material under conditions such that the target site material remains bound to the carrier; and
(e) recovering the target site-specific polyclonal antibody.

The specific concentrations of target site material bound to the carrier, and polyclonal antibody, as well as such parameters as incubation time for binding of polyclonal antibody and elution conditions, can be varied.

For example, the target site-specific polyclonal antibody can be absorbed to the target site bound to the carrier by incubating the polyclonal antibody and target site at 4°–37° C. for up to 24 hours. The absorbed polyclonal antibody can then be eluted from the carrier bound substance by such common techniques as use of an acidic solution, such as 0.1–1.0M glycine-HCl buffer at pH 2.0–5.0, or a chaotropic agent, such as 1.0–5.0M potassium thiocyanate at pH 4.0–7.5.

Those skilled in the art will know of many other suitable techniques for the purification of target site-specific polyclonal antibody, or will be able to ascertain such, using routine experimentation.

Monoclonal antibodies, when used in the present invention, can be produced in various ways using techniques well understood by those having ordinary skill in the art and will not be repeated here. Details of these techniques are described in such books as *Monoclonal Antibodies-Hybridomas: A New Dimension in Biological Analysis*, edited by Roger H. Kennet et al., published by Plenum Press (1980).

The term "couple" as utilized in the specification and claims is meant to include broadly the firm attachment of the activator to the antibody. Such attachment may be covalent or noncovalent, although it is preferably covalent. The coupling of the two entities may be direct or, most commonly, by means of a coupling or conjugating agent. There are several intermolecular cross-linking reagents which can be utilized (see, for example, Means, G. E. and Feeney, R. E., *Chemical Modification of Proteins*, Holden-Day, 1974, pp. 39–43). Among these reagents are, for example, N-succinimidyl 3-(2-pyridyldithio) propionate (SPDP) or N-N'-(1,3-phenylene) bismalemide (both are highly specific for sulfhydryls, and form irreversible linkages); N-N'-ethylene-bis-(iodoacetamide) or other such reagent having 6 and 11 carbon methylene bridges (relatively specific for sulfhydryl groups); 1,5-difluoro-2,4-dinitrobenzene (forms irreversible linkages with amino and tyrosine groups); p,p'-difluoro-m-m'-dinitrodiphenylsulfone (forms irreversible crosslinkages with amino and phenolic groups); dimethyl adipimidate (specific for amino groups); phenyl-2,4-disulfonylchloride (reacts principally with amino groups); hexamethylenediisocyanate or diisothiocyanate, or azophenyl-p-diisocyanate (reacting principally with amino groups); glutaraldehyde (reacting with several different side chains) and bisdiazobenzidine (reacting primarily with tyrosine and histidine). These are only a few of several cross-linking agents that can be utilized.

It is also possible for the activator to be coupled to the antibody through interactions occurring at the genetic level. For instance, an antibody/activator molecule could be produced wherein the hybridoma secretes an antibody which has had its Fc portion replaced with a different protein which functions as the activator (see, e.g., Neuberger, M. S. et al., *Nature*, 312:604 (1984)).

The conditions and concentrations useful for obtaining the antibody/activator couples of the invention can be readily adjusted by those of skill in the art by reference to known literature or by no more than routine experimentation.

The molar ratio of activator to antibody can vary from 1:1000 to 1000:1, more preferably 1:10 to 100:1, and most preferably 1:1 to 100:1.

In one embodiment of the present invention, the thrombolysis of blood clots, the antibodies usable in preparing the products of this embodiment may be any antibodies which are fibrin-specific and are substantially devoid of fibrinogen cross-reactivity. For example, antibodies with that specificity have been described in Hui, K. Y. et al., *Science*, 222:1129–1131 (1983). Further description of the same type of antibodies can be found in commonly assigned co-pending U.S. patent application Ser. No. 603,155, filed Apr. 23, 1984, by Gary R. Matsueda et al. for "Fibrin-Specific Monoclonal Antibodies Lacking Fibrinogen Cross-Reactivity," the entire contents of which are herein incorporated by reference.

The aforementioned co-pending patent application, for example, describes antibodies and methods of preparing the same of the specificity desired in the present invention, by providing peptides capable of raising such antibodies. These peptides generally are those comprising the formula:

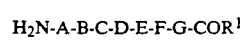

$$H_2N\text{-}A\text{-}B\text{-}C\text{-}D\text{-}E\text{-}F\text{-}G\text{-}COR^1$$

wherein A is glycine, B is histidine or proline, C is arginine, D is proline or valine, E is leucine or valine, F is aspartic acid or glutamic acid, and G is lysine or arginine;

$R^1$ is $R^2$; lys-CO-$R^2$; -lys-arg-CO-$R^2$ or -lys-arg-glu-CO-$R^2$;

$R^2$ is -cys-CO$R^3$, OH, OM, or $NR^4R^5$;

$R^3$ is OH, OM, or $NR^4R^5$;

M is a pharmaceutically acceptable cation or a lower branched or unbranched alkyl group; $R^4$ and $R^5$ are the same or different and are selected from the group consisting of H or a lower alkyl group.

These peptides, which are only given herein as illustration and are not the only ones which can be used in this embodiment of the invention, are 7-11 peptides and are utilized in sensitization and/or immunization, cell fusion, ascites production, selection of mixed hybridomas and/or subcloning of hybridomas to produce polyclonal monospecific or monoclonal antibodies. The peptides, which contain fibrin-specific sequences, are attached to an immunogenic protein through a connecting bridge, such as maleimidobenzoylated (MB)-keyhole limpet hemocyanine (KLH). Immunized animals or cells obtained therefrom can be used as a source to obtain monospecific antibodies followed by subsequent affinity chromatography using fibrinogen as a ligand, or may be fused to produce hybridomas to secrete antifibrin-specific monoclonal antibodies with substantially no cross-reactivity to fibrinogen.

Generally, any antibody obtained by using these or other peptides as immunogens can be utilized for this embodiment. Among the preferred ones are monoclonal antibodies obtained from cell line 59D8 on deposit at the ATCC with Accession No. HB8546, cell line 64C5 on deposit at the ATCC with Accession No. HB8545, and cell line 55D10 on deposit at the ATCC with Accession No. HB8547. These lines were placed on deposit at the ATCC prior to Apr. 23, 1984.

Other antibodies of the desired specificity are obtained by using as immunogen the amino terminus of the alpha chain of fibrin, or by immunizing with fibrin and then selecting a subset by affinity chromatography using fibrinogen as a ligand.

By the term "thrombolytic agent" as used in the present specification and claims is meant to include broadly any agent utilized for or inducing or initiating the lysis of a thrombus. The most common agents are urokinase, streptokinase and tissue-type plasminogen activator (TPA). Nevertheless, the obtainment of great selectivity observed with the antibodies utilized in the present invention, indicates that any other such thrombolytic agents can be utilized.

Coupled products of the overall invention can also be used as pharmaceutical compositions.

For example, the coupled products of the invention can be formulated in appropriate pharmaceutical compositions by including activating amounts of the desired product together with pharmacologically appropriate carriers. Generally speaking, these carriers include aqueous or alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases, and the like. See, generally, *Remington's Pharmaceutical Sciences*, 16th Ed., Mack, eds. 1980.

The route of administration of pharmaceutical compositions prepared according to the method of the invention may be any of those commonly known to those of ordinary skill in the art.

For therapy, including without limitation thrombolytic therapy, the coupled products of the invention can be administered to any patient in need of such therapy. The administration can be by any appropriate mode, including parenteral, intravenous, intramuscular, intraperitoneal, or, also appropriately, by direct infusion with a catheter, such as in intracoronary administration. The dosage and frequency of administration will depend on the age, sex and condition of the patient, concurrent administration of other drugs, counter indications and other parameters to be taken into account by the clinician.

The exact dosage and frequency with which the coupled products of the invention would be administered when used as therapeutic compositions are known to those of ordinary skill in the art or are readily ascertainable with only minor experimentation.

For example, when pharmaceutical compositions of the invention are used in therapy, the dosages and frequency of administration can be comparable to those used for the administration of the active substance, or of the activator itself in the prior art. Generally, however, the dosage will be from about 0.001 to 0.2 times the dosage normally utilized for the administration of the active substance by itself.

For example, for a urokinase/antibody complex, the administration for systemic fibrinolysis (pulmonary embolism) values for a 75 kilogram person will be:

1. Loading dose: broad range: 150 to 66,000 units over 10 minutes; intermediate range: 330 to 30,000 units over 10 minutes.
2. Maintenance dose: broad range: 187.5 to 66,000 units per hour for. 12 to 24 hours; intermediate range: 330 to 37,500 units per hour for 12 to 24 hours resulting in 2,400–1,650,000 total units (Sharma et al., NEJM, 306:1268–1276 (1982).

For a urokinase/antibody complex, the intracoronary administration dosage will be:

1. No loading dose.
2. 6–1,200 units per minute for 60–120 minutes resulting in a total of 360–144,000 units solution of 1.5–300 units per ml (Tennant et al., *Circulation*, 69:756–760 (1984)).

For a streptokinase/antibody complex, the systemic intracoronary administration dosage will be:

1. Loading dose: 250–50,000 units.
2. Maintenance dose: 100–20,000 units per hour for 24 hours or boluf injection of 5,000–300,000 units over 30 to 60 minutes.

For a streptokinase/antibody complex, the intracoronary administration dosage will be:

1. Loading dose 0.01–6,000 units in 3 ml 5% dextrose over 2 minutes.
   Maintenance dose: 5–1,000 units in one ml 5% dextrose up to maximal dose (500 to 100,000 units) (Laffel and Braunwald, NEJM, 311: 710–717 (1984)).

In the aforementioned dosage descriptions, the term "units" refers to the known and established definitions utilized for the activity of the thrombolytic agents in the prior art.

Having now generally described this invention, the same will be better understood by reference to one or more specific examples. These examples are included herein for purposes of illustration only and are not intended to be limiting unless otherwise specified.

EXAMPLE 1

A. Preparation of Urokinase-Antibody Conjugate

Reduced urokinase was coupled to fibrin-specific monoclonal antibody 64C5 via its intrinsic sulfhydryl groups utilizing N-succinimidyl 3-(2-pyridyldithio) propionate (SPDP) groups as a cross-linking agent (Carlsson, J. et al., *Biochem. J.*, 173:723–737 (1978)). SPDP (20 mM in 0.05 ml absolute ethanol) was added to the antibody (6.3 mg in 3.0 ml of 0.01M sodium phosphate, 0.1M NaCl, pH 7.4 (PBS)) and the mixture allowed to react for 30 minutes at room temperature. The solution was subsequently dialyzed against three one-liter changes of PBS. Analysis for 2-pyridyldisulfide content (Grassetti, D. R. and Murray, J. F., *Archives of Biochemistry and Biophysics,* 119:41–49 (1967) and Stuchbury, T. et al., *Biochem. J.,* 151:417–432 (1975)) showed 10.8 residues per antibody molecule. Urokinase (7 mg, 3.5 mg/ml in 0.1M sodium acetate, 0.1M NaCl, pH 4.5) was trace-labeled by addition of 20 uCi 125-I urokinase (0.03 mg in 0.3 ml PBS containing 0.03% $NaN_3$ (PBSA) (Greenwood, F. C. et al., *Biochem. J.,* 89:114–123 (1963)). The mixture was reduced by addition of 0.23 ml 1.0M dithiothreitol in 0.1M sodium acetate, 0.1M NaCl, pH 4.5, for 30 minutes at room temperature and desalted on Sephadex G 25 (0.7×25 cm) equilibrated with PBSA pH 4.5. Peak fractions from the column were pooled (4.3 ml, containing 1.1. mg/ml protein (Lowry, O. H. et al., *J. Biol. Chem.,* 193:265–275 (1951) and mixed with PDP-antibody (2.9 ml, containing 2.1 mg/ml protein (ibid)). The mixture was neutralized and allowed to react overnight. Under these conditions, the intrinsic sulfhydryl groups of the urokinase chains react with the pyridyldisulfide groups of the modified antibody, resulting in displacement of thiopyridine and formation of disulfide-containing intermolecular bridge.

Unconjugated urokinase and its component subunits were separated from the urokinase-antibody conjugate (125 I-UK)-SS-(64C5) by gel filtration on Sephacryl S-200 (2.5×90 cm). Two radioactive fractions were clearly resolved. The first contained the antibody-urokinase conjugate and was free of unconjugated urokinase. By SDS-PAGE, its molecular size exceeded 150 KD and it proved to be radioactive on subsequent autoradiography, indicating that it contained the urokinase subunit. The incorporation of urokinase averaged one mole per 3 of antibody as determined by specific radioactivity of the urokinase subunit. Further evidence of the association of urokinase activity with antibody was obtained by affinity chromatography of the antibody-urokinase conjugate on a column constructed by coupling a synthetic amino terminal beta chain fibrin peptide (Gly-His-Arg-Pro-Leu-Asp-Lys-Cys (Hui, K. Y. et al., *Science,* 222: 1129–1131 (1983)) (BPEPTIDE) to N-Maleimido-Benzoyl-Lysine-Sepharose CL-4B (Kitagawa, T. and Aikawa, T., *J. Biochem* (Japan), 79: 233 (1976)). The eluate of this column (0.2M glycine HCl, pH 2.8) was radioactive and fibrinolytic in the assay described below (both properties of urokinase). The same methods were used to synthesize and purify a conjugate of urokinase and myosin-specific monoclonal antibody 3H3 (I-UK)-SS-(3H3) (Khaw, B. A. et al., *Hybridoma,* 3:11–23 (1984)).

B. Assay for Fibrinolytic Activity

A quantitative fibrinolytic assay was devised by linking fibrin monomer to Sepharose. Kabi grade L fibrinogen (500 mg) was dissolved in 50 mM phosphate buffer, pH 7.4 and then passed over lysine-Sepharose to eliminate traces of plasminogen. The purified fibrinogen was trace-labeled by the addition of 150 uCi 125-I fibrinogen (IBRIN) and the mixture coupled to 150 ml cyanogen bromide activated Sepharose 4B-Cl. After thorough washing, the gel was suspended in 0.1M Tris, 0.15M NaCl, 0.02% $NaN_3$, pH 7.4 (TBSA) and the immobilized fibrinogen converted to fibrin by addition of human thrombin (1 NIH unit/ml) in the presence of 100 mM $CaCl_2$. After 4 liters of washing, 125-I fibrin-Sepharose was stored in TBSA at 0 degrees. The substituted Sepharose was stable, releasing 0.1% of its radioactivity at 2.5 hours and 2.1% at 15 hours on incubation in the absence of urokinase-containing conjugates.

To assess their relative fibrinolytic activity, increasing amounts of (125 I-UK)-SS-(64C5) and unconjugated urokinase were incubated with 100 ul of 125 I-fibrin-Sepharose for 4 hours. The Sepharose was then washed first with 3 ml of a solution comprising 0.1M Tris, 0.1M NaCl, 0.5% bovine serum albumin and 0.5% Triton X-100 and then with three 3 ml aliquots of TBSA. Thereafter, the resin was incubated at room temperature with purified plasminogen (Deutsch, D. G. et al., *Science,* 170:1095–1096 (1970)) (0.15 mg/ml) in 50 mM phosphate buffer, pH 7.4. After either 2.5 or 15 hours, the mixture was centrifuged and the radioactivity of the supernatant determined in a gamma scintillation counter. This procedure was repeated with (125 I-UK)-SS-(3H3).

In order to obtain kinetic information (125 I-UK)-SS-(3H3), or (125 I-UK)-SS-64C5 in TBSA containing 0.12 mg/ml plasminogen were recirculated over a (0.3×5 cm) column containing 300 ul 125 I fibrin-Sepharose at a rate of 1 ml per minute. At indicated times, three samples of 1 ml each were collected and their radioactivity determined.

Figure 2:
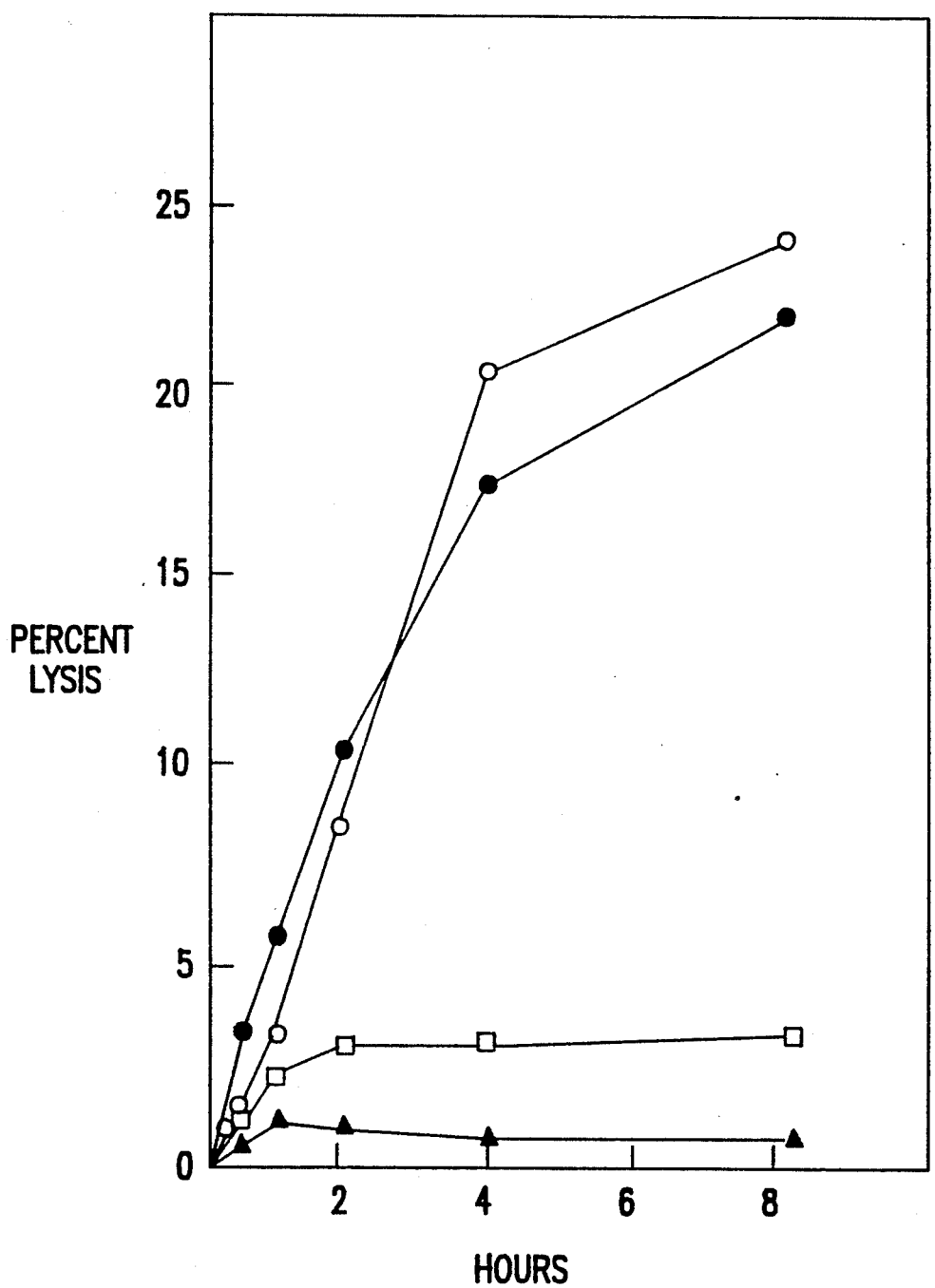
FIG. 2 shows the release of labeled peptides from fibrin-Sepharose during recirculation of a solution containing plasminogen (0.12 mg/ml) and fibrin-specific antibody 64C5 in the presence (○) and absence (●) of 3.5 mg/ml fibrinogen. The experiment was repeated with a myosin-specific antibody (3H3) in the presence (▲) and absence (□) of fibrinogen. In each instance, the recirculating fluid contained 0.25 units of urokinase activity/ml coupled to either of the antibodies. Each point represents the mean of three determinations with a standard deviation of less than 1.6%.

FIG. 1 indicates that the concentration of (125 I-UK)-SS-(64C5) required to release labeled peptides from fibrin-Sepharose was 1/100 of that of unconjugated urokinase. The myosin antibody conjugate (125 I-UK)-SS-(3H3) did not differ significantly from unconjugated urokinase. FIG. 2 shows that (125 I-UK)-SS-(64C5) markedly enhances the rate of release of peptides from fibrin-Sepharose and that this is unimpaired by fibrinogen at a physiologic concentration. BPeptide inhibits fibrinolysis of (125 I-UK)-SS-(64C5), whereas it has no effect on the fibrinolytic rate of unconjugated urokinase or (125 I-UK)-SS-(3H3) (data not shown).

C. Conclusions

A monoclonal antibody specific for fibrin is able to target the plasminogen activator urokinase to fibrin and by virtue of enhanced local concentration, increase the efficiency of plasmin lysis by 100-fold. The antibody is sufficiently fibrin-specific so that physiologic effects of fibrinogen do not interfere with enhanced fibrinolysis. Fibrinolytic effectiveness is not enhanced by coupling of urokinase to a monoclonal antibody of irrelevant specificity but it is markedly diminished by a peptide representing the epitope recognized by the fibrin-specific antibody.

Having now fully described this invention, it will be appreciated that the same can be performed within a wide and equivalent range of parameters, conditions, modes of administration, conjugates, antibodies, activating agents, and the like without affecting the spirit or scope of the invention or of any embodiment therein.

What is claimed as new and is desired to be covered by United States Letters Patent is:

1. A method of lysing a thrombus in a host, said method comprising:

administering to said host a conjugate consisting of a monoclonal antibody specific for fibrin and devoid of cross-reactivity with fibrinogen, said antibody coupled to a plasminogen activator, wherein upon contact with a thrombus said conjugate lyses the thrombus via the action of said plasminogen activator.

2. The method of claim 1 wherein said plasminogen activator is selected from the group consisting of urokinase, streptokinase and tissue type plasminogen activator.

* * * * *